United States Patent [19]

Bilbee et al.

[11] 4,019,020
[45] Apr. 19, 1977

[54] CONTROLLED TEMPERATURE FLUID HEATER

[75] Inventors: Larry T. Bilbee; Thomas L. Clabaugh, both of Bellville, Ohio

[73] Assignee: The Gorman-Rupp Company, Mansfield, Ohio

[22] Filed: Aug. 13, 1975

[21] Appl. No.: 604,339

[52] U.S. Cl. .......................... 219/302; 128/214 A; 128/399; 165/46; 219/298; 219/299; 219/308; 222/146 HE

[51] Int. Cl.² ...................... A61M 5/14; F24H 1/12; B67D 5/62; F28F 7/00

[58] Field of Search .......................... 219/296–299, 219/301–309, 214, 535; 128/399, 214 R, 214 A; 165/46; 222/146 R, 146 H, 146 HS, 146 HA, 146 C, 146 HE

[56] References Cited
UNITED STATES PATENTS

| | | | |
|---|---|---|---|
| 1,492,821 | 5/1924 | Weinbach | 219/535 X |
| 3,140,716 | 7/1964 | Harrison et al. | 219/301 UX |
| 3,443,060 | 5/1969 | Smith | 219/305 X |
| 3,485,245 | 12/1969 | Lahr et al. | 219/302 UX |
| 3,590,215 | 6/1971 | Anderson et al. | 165/46 X |

Primary Examiner—A. Bartis
Attorney, Agent, or Firm—Hamilton, Renner & Kenner

[57] ABSTRACT

An apparatus for maintaining a fluid supply, such as human blood going to a hospital patient, at optimum temperatures comprises an electrically heated inner mandrel maintained at a thermostatically controlled temperature. A substantially flat plastic bag having sealed linear forming labyrinth liquid flow passageways is wrapped around the mandrel and supply and exhaust tubes are connected to the ends of the passageways. An outer housing having a pair of hinged wings is provided for holding the bag in wrapped-around contact with the mandrel. The linear sealed areas are interrupted by spaced gaps adapted to inhibit the accumulation of air bubbles along the sealed linear areas.

4 Claims, 7 Drawing Figures

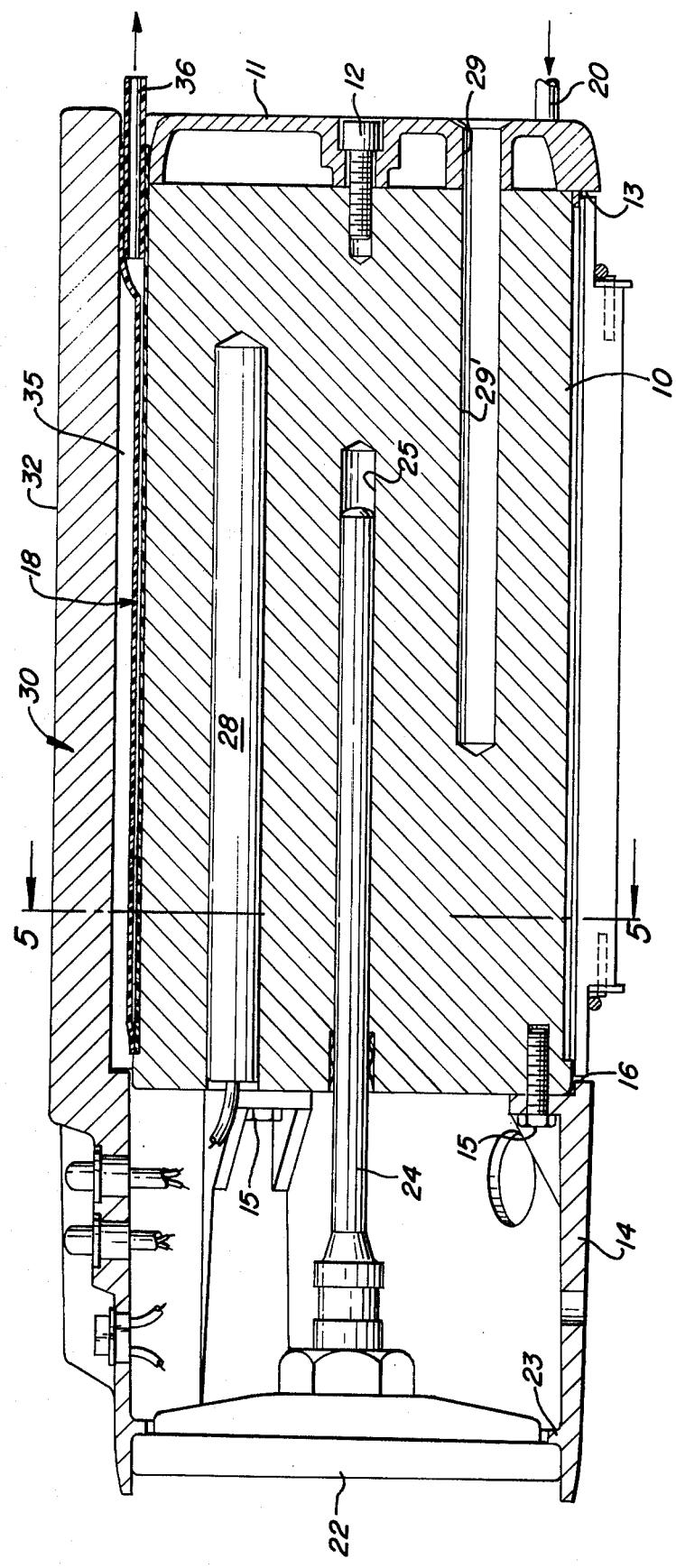
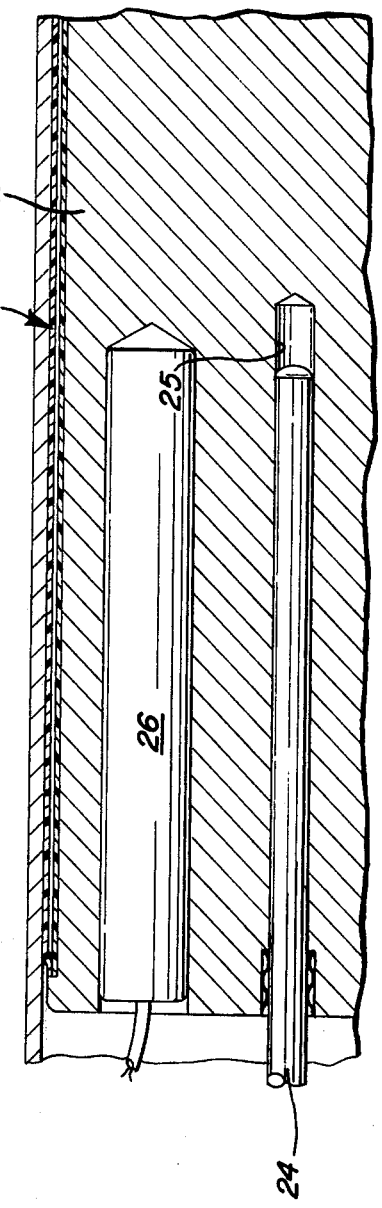
FIG. 3
FIG. 4

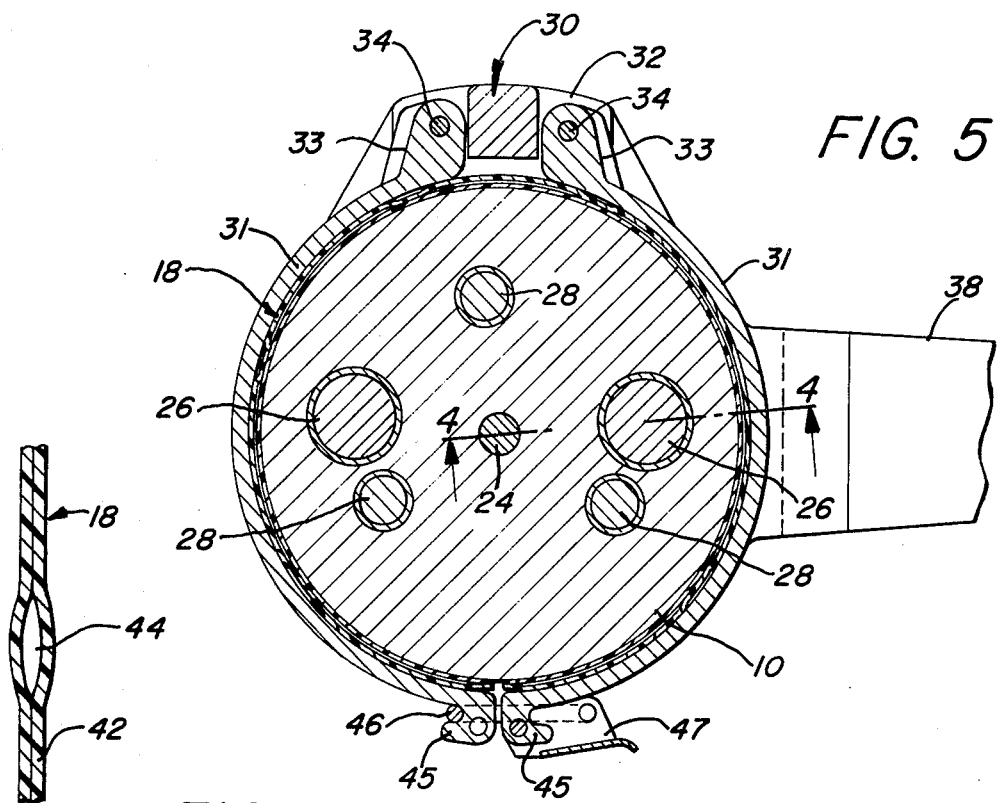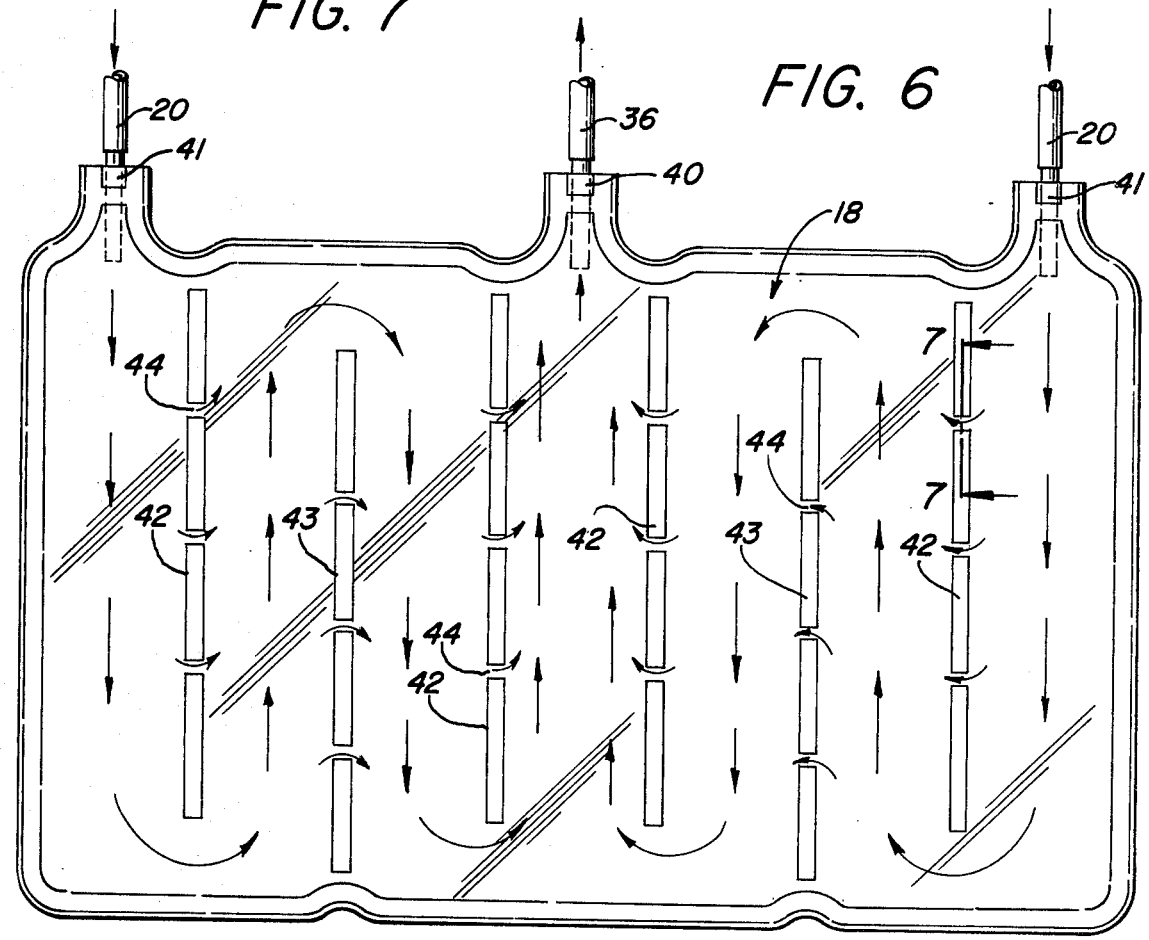

CONTROLLED TEMPERATURE FLUID HEATER

BACKGROUND OF THE INVENTION

In prior U.S. Pat. No. 3,443,060, a plastic bag carrying blood for a patient was maintained at a thermostatically controlled temperature by a cylindrical heated mandrel around which a flat plastic bag was telescoped, and an outer hollow cylindrical mandrel was telescoped over the bag on the inner mandrel. Longitudinal ribs formed on one of the mandrels pressed the bag walls together under the ribs and restricted the bag to form a labyrinth of passageways through the bag, with inlet and outlet connections for conducting the blood supply to the bag and from the bag to the patent.

Properly inserting and fitting the bag between the inner and outer mandrels in the construction of prior patent No. 3,443,060 is a difficult and time-consuming operation, and the particular shape of the bag is costly to fabricate.

SUMMARY OF THE INVENTION

It is an object of the present invention to provide an improved fluid heating device having a plastic bag which is quickly and easily positioned around an inner heated cylindrical mandrel and held within an outer housing having hinged doors for quick opening and closure.

Another object is to provide an improved fluid heating device having a plastic bag with its walls sealed together along linear areas interrupted by narrow gaps designed to inhibit the accumulation of air along said linear areas.

A further object is to provide an improved fluid heating device having an inner heated cylindrical mandrel and an outer housing comprising a longitudinal arm and two semicylindrical housing doors or wings hinged thereto for holding a plastic bag around said mandrel.

These and other objects are accomplished by the improvements comprising the present invention, a preferred embodiment of which is shown by way of examle in the accompanying drawings, and hereinafter described in detail. Various modifications and changes in details of construction are comprehended within the scope of the appended claims.

BRIEF DESCRIPTION OF THE DRAWINGS

FIG. 3 is a longitudinal sectional view on line 3—3 of FIG. 1.

FIG. 4 is a partial sectional view on line 4—4 of FIG. 5.

FIG. 5 is a cross-sectional view on line 5—5 of FIG. 3.

FIG. 6 is a plan view of the flat bag detached from the assembly.

FIG. 7 is a partial sectional view on line 7—7 of FIG. 6.

DESCRIPTION OF A PREFERRED EMBODIMENT

Figure 1:
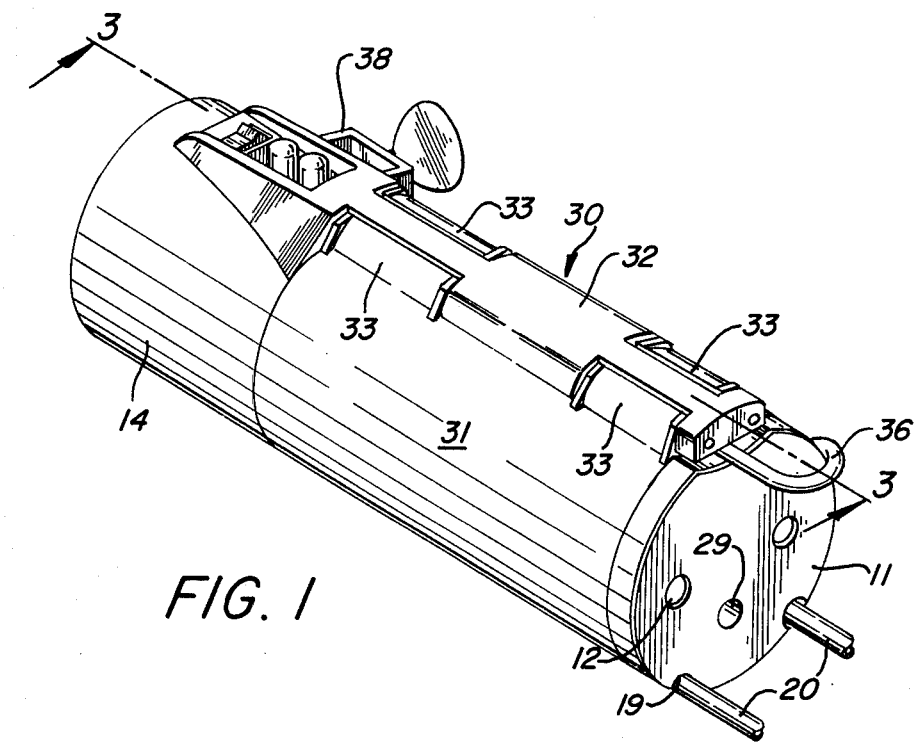
FIG. 1 is a perspective view of the improved fluid heating device with the bag held within the closed housing.

Referring to FIGS. 2 – 5, the inner mandrel 10 is preferably substantially cylindrical and made of a metal of high thermal conductivity such as aluminum. A cap 11 is secured by a screw 12 to the rear end of the mandrel and its outer periphery forms a circumferential shoulder 13 adjacent the outer end of the mandrel. A substantially cylindrical cover 14 is attached to the front end of mandrel 10 by screws 15 and its outer periphery forms a circumferential shoulder 16 adjacent the inner end of the mandrel.

The flat plastic bag 18 (FIG. 6) is designed to wrap around and fit over the mandrel between the shoulders 13 and 16, and the end cap 11 has peripheral notches 19 to receive fluid supply tubes 20 connected to the bag 12.

The front end of cover 14 is adapted to receive a circular temperature gauge 22 (FIG. 3) which abuts a circumferential internal rib 23 on the cover and is readable from the front end of the cover. The gauge has a temperature sensing element 24 extending into an axial bore 25 in the inner mandrel 10. Thermostat rods 26 are inserted into longitudinal bores in the mandrel 10 arranged around the sensing rod 24, and cartridge type heating elements 28 are inserted into longitudinal bores in the mandrel.

The temperature of the mandrel 10 is controlled in the same manner as in prior U.S. Pat. No. 3,443,060, the thermostats 26 being electrically connected in series with the electrical heaters 28, to maintain the mandrel at about 100° F., and preferably an alternate thermostat is connected to take over if the other fails to function. The cap 11 preferably has an aperture 29 which registers with a calibration well 29' for checking the temperature of the mandrel.

The cover 14 has an upper bar 30 extending rearwardly over the top of the mandrel 10 for hingedly supporting the semicylindrical wings 31 forming the doors of the outer housing adapted to hold the bag 18 wrapped around the mandrel 10. The bar 30 has a central portion 32 with front and rear recessed portions adjacent thereto for receiving the longitudinally spaced ears 33 on the upper edges of the wings 31. Hinge pins 34 are then inserted through aligned longitudinal bores in the ears 33 and in the ends and central portion 32 of the bar to hingedly mount the wings on the bar. A groove 35 is provided between the underside of the bar 30 and the mandrel 10 and end cap 11 to accommodate an exhaust tube 36 connected to the bag 18. The rear ends of the wings 31 are provided near their bottom edges with notches 37 to accommodate the connections between the fluid supply tubes 20 and the bag 18. A support bracket 38 may be provided on one side of the cover for attachment to a suitable support maintaining the assembly in substantially horizontal position.

Referring to FIGS. 6 and 7, the normally flat bag 18 is a two-ply plastic bag which is substantially rectangular with sealed outer edges and a central port 40 and two end ports 41 communicating with the chamber formed between the plies. The ports 41 are adapted to be connected to the fluid supply tubes 20 and the port 40 to the exhaust tube 36. A labyrinth of connected passageways is formed within the bag by sealing the walls or plies thereof along linear areas or grooves indicated at 42 and 43, the grooves being spaced apart laterally and longitudinally parallel to the axes of the ports 40 and 41.

Thus, fluid introduced through supply ports 41 will flow successively around the far ends of grooves 42 and around the near ends of grooves 43 to the exhaust port 40. The linear sealed areas 42 and 43 are intermittent, that is, they are separated by narrow gaps or unsealed areas 44 which provide some slight communication between the passageways on opposite sides of the linear sealed areas.

Inasmuch as the fluid heater assembly is positioned horizontally when in use, the linear sealed areas are also horizontally disposed. Accordingly, small air bubbles in the fluid supply tend to accumulate along the lower edges of the sealed linear areas with accompanying stagnation or lack of proper circulation of the fluid at those locations. Also, the accumulation of bubbles diminishes the heat transfer from the mandrel to the fluid. The unsealed gaps 44 between the sealed areas allow some slight flow-through between the adjacent flow passageways and thus greatly inhibit the accumulation of air and stagnation of flow along the sealed areas.

Figure 2:
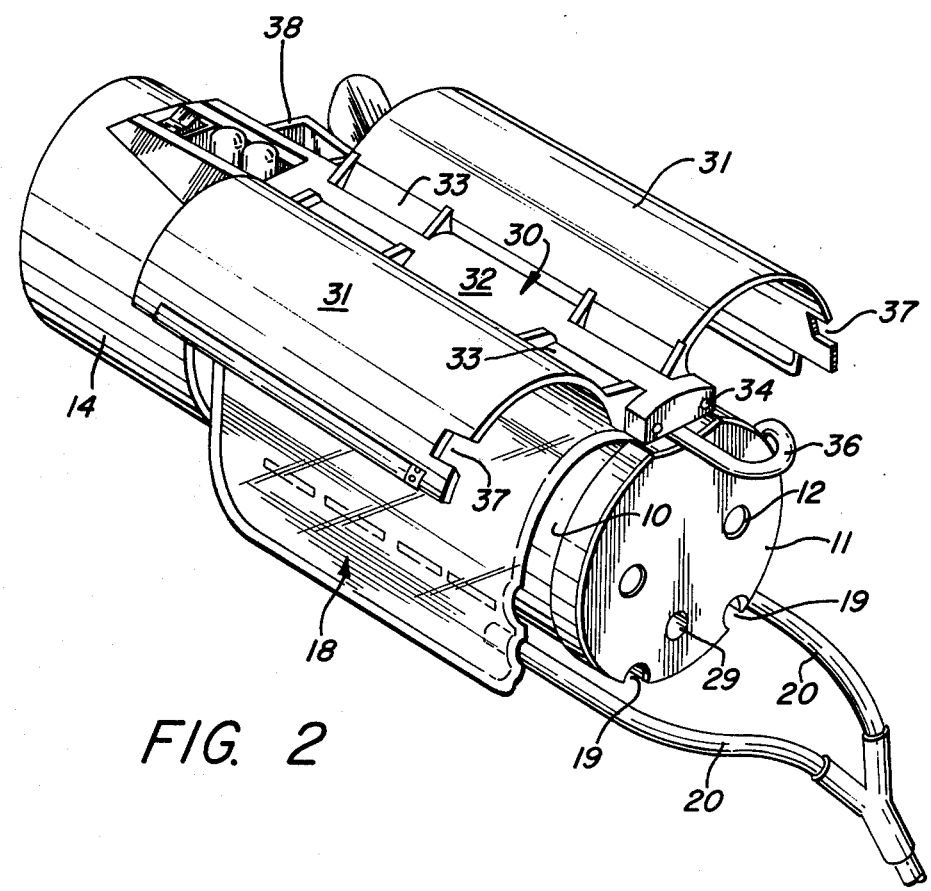
FIG. 2 is a similar view showing the housing wings unclamped and swung open.

When the flat bag 18 is positioned around the mandrel 10 in the manner shown in FIG. 2 and the supply tubes 20 and exhaust tube connected thereto, the wings 31 are swung downwardly until their flanged lower edges 45 abut each other thus maintaining a fixed space for containing the bag between the mandrel and the cover 14, as shown in FIG. 5. In this position a wire clip 46 pivoted in one flange 45 is snapped over and behind the other flange by means of handle 47 to detachably secure the flanged edges together.

In the operation of the improved fluid heater, for example as applied to maintaining at optimum temperature a blood supply to a human patient in a hospital, the blood flows through the supply tubes 20 and circulates through the passageways formed in the bag 18 by the sealed linear areas 42 and 43 wherein it is heated to optimum temperature by the heated mandrel 10. The heated blood then flows through the exhaust tube 36 and a conventional air bubble trap to the patient. The flat bag 18 may be replaced easily and quickly by unclamping the botton wing flanges and swinging them to the open position of FIG. 2.

We claim:

1. Apparatus for maintaining a flow of fluid at optimum temperature comprising an inner mandrel having high thermal conductivity, means for maintaining said inner mandrel at constant optimum temperature, a substantially flat plastic bag wrapped around said inner mandrel and having sealed linear areas forming a labyrinth of passageways through the bag, said sealed linear areas being interrupted by gaps adapted to inhibit the accumulation of air bubbles along the sealed linear areas, and an outer housing havng hinged wings for holding said bag in wrapped-around contact with said inner mandrel when their free edges are secured in abutment with each other.

2. Apparatus for maintaining a flow of fluid at optimum temperature comprising an inner mandrel having high thermal conductivity, means for maintaining said inner mandrel at constant optimum temperature, a substantially flat plastic bag wrapped around said inner mandrel and having sealed linear areas forming a labyrinth of passageways through the bag, said bag having supply tubes and an exhaust tube on one side connected to said passageways, a stationary cover portion secured to one end of said mandrel and adapted to hold and support the mandrel during use, an elongated arm fixedly secured to said stationary cover portion and extending longitudinally along substantially the length of the portion of the mandrel covered by the bag with the arm radially spaced from the mandrel to accommodate said exhaust tube, and an outer housing having wings hinged to opposite sides of said arm for holding said bag in wrapped-around contact with said inner mandrel when their free edges are secured in abutment with each other, said wings having notches at one end to accommodate said supply tubes.

3. Apparatus as defined in claim 2, in which the inner mandrel and the wings are substantially cylindrical and the sealed linear areas in the bag run longitudinally of the inner mandrel.

4. Apparatus as defined in claim 3, in which the sealed linear areas are interrupted by gaps adapted to inhibit the accumulation of air bubbles along the sides of the sealed linear areas.

* * * * *